(12) United States Patent
Adler et al.

(10) Patent No.: US 6,331,413 B1
(45) Date of Patent: Dec. 18, 2001

(54) SECRETED SALIVARY ZSIG63 POLYPEPTIDE

(75) Inventors: David A. Adler, Bainbridge Island; Paul O. Sheppard, Granite Falls, both of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/527,345

(22) Filed: Mar. 17, 2000

Related U.S. Application Data

(60) Provisional application No. 60/124,820, filed on Mar. 17, 1999.
(51) Int. Cl.[7] .............................. C12P 21/06; C12N 1/12; C12N 15/00; C12N 5/00; C07H 21/02
(52) U.S. Cl. ...................... 435/69.1; 435/320.1; 435/325; 435/252.3; 435/6; 536/23.1; 536/23.5
(58) Field of Search ................................ 435/69.1, 320.1, 435/252.3, 6.325; 536/23.5

(56) References Cited

FOREIGN PATENT DOCUMENTS

9901466 * 1/1999 (WO).

* cited by examiner

*Primary Examiner*—Rebecca E. Prouty
*Assistant Examiner*—Maryam Monshipouri
(74) *Attorney, Agent, or Firm*—Jennifer K. Johnson, JD

(57) ABSTRACT

The present invention relates to polynucleotide and polypeptide molecules for zsig63, a novel secreted salivary protein. The polypeptides, and polynucleotides encoding them, may exhibit anti-microbial activity and may be used in the study or treatment of microbial infections. The polynucleotides encoding zsig63, are located on chromosome 4, and can be used to identify a region of the genome associated with human disease states. The present invention also includes antibodies to the zsig63 polypeptides.

9 Claims, No Drawings

SEQUENCE LISTING

```
<160> NUMBER OF SEQ ID NOS:  9

<210> SEQ ID NO 1
<211> LENGTH: 1008
<212> TYPE: DNA
<213> ORGANISM: Homo sapiens
<220> FEATURE:
<221> NAME/KEY: CDS
<222> LOCATION: (128)...(784)

<400> SEQUENCE: 1
agacagacta aaaaagccat gtattctttc gtttctctct aaaagaagaa aaatataatt      60
taaaaataca ttgcgtattt tctaaaacaa taaatttata gtgttaatat tcatagggtc     120
```

```
aatcaaa atg aag ctt ctc ctt tgg gcc tgc att gta tgt gtt gct ttt        169
        Met Lys Leu Leu Leu Trp Ala Cys Ile Val Cys Val Ala Phe
         1               5                  10 gca agg aag aga cgg ttc ccc ttc att ggt gag gat gac aat gac gat        217
Ala Arg Lys Arg Arg Phe Pro Phe Ile Gly Glu Asp Asp Asn Asp Asp
 15              20                  25                  30 ggt cac cca ctt cat cca tct ctg aat att cct tat ggc ata cgg aat        265
Gly His Pro Leu His Pro Ser Leu Asn Ile Pro Tyr Gly Ile Arg Asn
                 35                  40                  45 tta cca cct cct ctt tat tat cgc cca gtg aat aca gtc ccc agt tac        313
Leu Pro Pro Pro Leu Tyr Tyr Arg Pro Val Asn Thr Val Pro Ser Tyr
             50                  55                  60 cct ggg aat act tac act gac aca ggg tta cct tcg tat ccc tgg att        361
Pro Gly Asn Thr Tyr Thr Asp Thr Gly Leu Pro Ser Tyr Pro Trp Ile
                 65                  70                  75 cta act tct cct gga ttc ccc tat gtc tat cac atc cgt ggt ttt ccc        409
Leu Thr Ser Pro Gly Phe Pro Tyr Val Tyr His Ile Arg Gly Phe Pro
 80                  85                  90 tta gct act cag ttg aat gtt cct cct ctc cct cct agg ggt ttc ccg        457
Leu Ala Thr Gln Leu Asn Val Pro Pro Leu Pro Pro Arg Gly Phe Pro
 95                 100                 105                 110 ttt gtc cct cct tca agg ttt ttt tca gca gct gca gca ccc gct gcc        505
Phe Val Pro Pro Ser Arg Phe Phe Ser Ala Ala Ala Ala Pro Ala Ala
                115                 120                 125 cca cct att gca gct gag cct gct gca gct gca cct ctt aca gcc aca        553
Pro Pro Ile Ala Ala Glu Pro Ala Ala Ala Ala Pro Leu Thr Ala Thr
                130                 135                 140 cct gta gca gct gag cct gct gca ggg gcc cct gtt gca gct gag cct        601
Pro Val Ala Ala Glu Pro Ala Ala Gly Ala Pro Val Ala Ala Glu Pro
            145                 150                 155 gct gca gag gca cct gtt gga gct gag cct gct gca gag gca cct gtt        649
Ala Ala Glu Ala Pro Val Gly Ala Glu Pro Ala Ala Glu Ala Pro Val
160                 165                 170 gca gct gag cct gct gca gag gca cct gtt gga gtg gag cca gct gca        697
Ala Ala Glu Pro Ala Ala Glu Ala Pro Val Gly Val Glu Pro Ala Ala
175                 180                 185                 190 gag gaa cct tca cca gct gag cct gct aca gcc aag cct gct gcc cca        745
Glu Glu Pro Ser Pro Ala Glu Pro Ala Thr Ala Lys Pro Ala Ala Pro
                195                 200                 205 gaa cct cac cct tct ccc tct ctt gaa cag gca aat cag tgaaattctc        794
Glu Pro His Pro Ser Pro Ser Leu Glu Gln Ala Asn Gln
                210                 215 tagaagagta ccatgggttc atttctatac tgatgcagaa ataagtgaaa tctacaaaag        854
ttttctttct tttccaaaga ctatttcatt ctgttgtatt cagagtattc atctcactac        914
attgatttgt ttgtggtagt ttttccttgg acttaattta tattgaaaaa acattgataa        974
ttaaataaat aaaatagata atttagacca atgg        1008

<210> SEQ ID NO 2
<211> LENGTH: 219
<212> TYPE: PRT
<213> ORGANISM: Homo sapiens

<400> SEQUENCE: 2

Met Lys Leu Leu Leu Trp Ala Cys Ile Val Cys Val Ala Phe Ala Arg
 1               5                  10                  15

Lys Arg Arg Phe Pro Phe Ile Gly Glu Asp Asp Asn Asp Asp Gly His
             20                  25                  30
```

```
Pro Leu His Pro Ser Leu Asn Ile Pro Tyr Gly Ile Arg Asn Leu Pro
         35                  40                  45

Pro Pro Leu Tyr Tyr Arg Pro Val Asn Thr Val Pro Ser Tyr Pro Gly
 50                  55                  60

Asn Thr Tyr Thr Asp Thr Gly Leu Pro Ser Tyr Pro Trp Ile Leu Thr
 65                  70                  75                  80

Ser Pro Gly Phe Pro Tyr Val Tyr His Ile Arg Gly Phe Pro Leu Ala
                 85                  90                  95

Thr Gln Leu Asn Val Pro Pro Leu Pro Pro Arg Gly Phe Pro Phe Val
             100                 105                 110

Pro Pro Ser Arg Phe Phe Ser Ala Ala Ala Pro Ala Ala Pro Pro
         115                 120                 125

Ile Ala Ala Glu Pro Ala Ala Ala Ala Pro Leu Thr Ala Thr Pro Val
     130                 135                 140

Ala Ala Glu Pro Ala Ala Gly Ala Pro Val Ala Ala Glu Pro Ala Ala
145                 150                 155                 160

Glu Ala Pro Val Gly Ala Glu Pro Ala Ala Glu Ala Pro Val Ala Ala
                165                 170                 175

Glu Pro Ala Ala Glu Ala Pro Val Gly Val Glu Pro Ala Ala Glu Glu
            180                 185                 190

Pro Ser Pro Ala Glu Pro Ala Thr Ala Lys Pro Ala Ala Pro Glu Pro
        195                 200                 205

His Pro Ser Pro Ser Leu Glu Gln Ala Asn Gln
    210                 215
```

<210> SEQ ID NO 3
<211> LENGTH: 657
<212> TYPE: DNA
<213> ORGANISM: Artificial Sequence
<220> FEATURE:
<223> OTHER INFORMATION: Degenerate polynucleotide sequence for zsig63
<221> NAME/KEY: misc_feature
<222> LOCATION: (1)...(657)
<223> OTHER INFORMATION: n = A,T,C or G

<400> SEQUENCE: 3

```
atgaarytny tnytntgggc ntgyathgtn tgygtngcnt tygcnmgnaa rmgnmgntty      60
ccnttyathg gngargayga yaaygaygay ggncayccny tncayccnws nytnaayath    120
ccntayggna thmgnaayyt ncncncncn ytntaytaym gnccngtnaa yacngtnccn     180
wsntayccng gnaayacnta yacngayacn ggnytnccnw sntayccntg gathytnacn    240
wsnccnggnt tyccntaygt ntaycayath mgnggnttyc cnytngcnac ncarytnaay    300
gtnccnccny tnccnccnmg nggnttyccn ttygtnccnc cnwsnmgntt yttywsngcn    360
gcngcngcnc cngcngcncc ncnathgcn gcngarccng cngcngcngc ncnytnacn      420 gcnacnccng tngcngcnga rccngcngcn ggngcnccng tngcngcnga rccngcngcn    480
gargcnccng tnggngcnga rccngcngcn gargcnccng tngcngcnga rccngcngcn    540
gargcnccng tnggngtnga rccngcngcn gargarccnw sncngcnga rccngcnacn     600 gcnaarccng cngcnccnga rccncayccn wsnccnwsny tngarcargc naaycar      657
```

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide primer ZC6768

```
<400> SEQUENCE: 4
gcaattaacc ctcactaaag ggaac                                      25

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer ZC694

<400> SEQUENCE: 5
taatacgact cactataggg                                            20

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide primer ZC7231

<400> SEQUENCE: 6
tttttttttt tttttttttt tttttv                                     26

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer ZC7764a

<400> SEQUENCE: 7
tttttttttt tttttttttt ttttta                                     26

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide primer ZC20555

<400> SEQUENCE: 8
ccacctcctc tttattat                                              18

<210> SEQ ID NO 9
<211> LENGTH: 18
<212> TYPE: DNA
<213> ORGANISM: Artificial Sequence
<220> FEATURE:
<223> OTHER INFORMATION: Oligonucleotide primer ZC20556

<400> SEQUENCE: 9
aatccaggag aagttaga                                              18
```

US 6,331,413 B1

SECRETED SALIVARY ZSIG63 POLYPEPTIDE

REFERENCE TO RELATED APPLICATIONS

This application is related to Provisional Application No. 60/124,820, filed on Mar. 17, 1999. Under 35 U.S.C. § 119(e)(1), this application claims benefit of said Provisional Application.

BACKGROUND OF THE INVENTION

Bacterial, and other microbial interaction with host tissues can have beneficial (symbiotic) as well as deleterious (pathogenic) consequences. Invading microbes can be pathogenic. Consequently, host biological defense strategies have evolved to protect organisms from invasion by disease-causing microorganisms.

Microbial infection response systems include oxidative and non-oxidative mechanisms, utilizing compounds that are enzymatically synthesized in cells, as well as peptides that are single gene products. For example, anti-microbial peptides constitute an oxygen-independent host defense system found in organisms encompassing many taxonomic families. One major class of anti-microbial peptides is defined by conserved cysteine residue patterns and is termed defensins. For example, mammalian defensins, derived from skin, lung and intestine, exhibit antibiotic activity against a wide variety of pathogens, including Gram-positive and Gram-negative bacteria, fungi (e.g., Candida species) and viruses. See, for example, Porter et al., *Infect. Immun.* 65(6): 2396–401, 1997.

A major class of microbial peptides is called adhesins. Adhesins enable microbes to adhere to mammalian tissues, for example the oral, gastrointestinal, urogenital and respiratory tracts. For a pathogenic microorganism, this may be a primary route to colonization and/or invasion of the host. Conversely, natural microbial flora can adhere to host tissues and create beneficial symbiotic relationships such as nutritional benefits, and protection against colonization of pathogenic microbes. The host defenses involved in attracting and establishing beneficial microbial colonization, as opposed to pathogenic microbial colonization, are not well understood. However, host defenses that affect this balance may have anti-microbial, immunomodulatory, inflammatory, anti-inflammatory or other properties.

Thus, moieties having anti-microbial, adhesin-like, immunomodulatory, inflammatory, anti-inflammatory or other properties are sought. The present invention provides such polypeptides for these and other uses that should be apparent to those skilled in the art from the teachings herein.

SUMMARY OF THE INVENTION

Within one aspect, the present invention provides an isolated polynucleotide encoding a zsig63 polypeptide comprising a sequence of amino acid residues that is at least 90% identical to an amino acid sequence selected from the group consisting of: (a) the amino acid sequence as shown in SEQ ID NO: 2 from amino acid number 16 (Arg) to amino acid number 37 (Ser); (b) the amino acid sequence as shown in SEQ ID NO: 2 from amino acid number 38 (Leu) to amino acid number 126 (Ala); (c) the amino acid sequence as shown in SEQ ID NO: 2 from amino acid number 127 (Pro) to amino acid number 219 (Gln); (d) the amino acid sequence as shown in SEQ ID NO:2 from amino acid number 16 (Arg) to amino acid number 219 (Gln); and (e) the amino acid sequence as shown in SEQ ID NO:2 from amino acid number 1 (Met) to amino acid number 219 (Gln). In one embodiment, the isolated polynucleotide disclosed above encodes a zsig63 polypeptide comprising a sequence of amino acid residues selected from the group consisting of: (a) the amino acid sequence as shown in SEQ ID NO: 2 from amino acid number 16 (Arg) to amino acid number 37 (Ser); (b) the amino acid sequence as shown in SEQ ID NO: 2 from amino acid number 38 (Leu) to amino acid number 126 (Ala); (c) the amino acid sequence as shown in SEQ ID NO: 2 from amino acid number 127 (Pro) to amino acid number 219 (Gln); (d) the amino acid sequence as shown in SEQ ID NO:2 from amino acid number 16 (Arg) to amino acid number 219 (Gln); and (e) the amino acid sequence as shown in SEQ ID NO:2 from amino acid number 1 (Met) to amino acid number 219 (Gln). In another embodiment, the isolated polynucleotide disclosed above is selected from the group consisting of: (a) a polynucleotide sequence as shown in SEQ ID NO:1 from nucleotide 173 to nucleotide 784; (b) a polynucleotide sequence as shown in SEQ ID NO:1 from nucleotide 128 to nucleotide 784; and (c) a polynucleotide sequence complementary to (a) or (b). In another embodiment, the isolated polynucleotide disclosed above comprises nucleotide 1 to nucleotide 657 of SEQ ID NO:3.

Within another aspect, the present invention provides an expression vector comprising the following operably linked elements: a transcription promoter; a DNA segment encoding a zsig63 polypeptide comprising an amino acid sequence that is at least 90% identical to the amino acid sequence shown in SEQ ID NO:2 from amino acid number 16 (Arg) to amino acid number 219 (Gln); and a transcription terminator. In one embodiment, the expression vector disclosed above further comprises a secretory signal sequence operably linked to the DNA segment.

Within another aspect, the present invention provides a cultured cell into which has been introduced an expression vector as disclosed above, wherein the cell expresses a polypeptide encoded by the DNA segment.

Within another aspect, the present invention provides a DNA construct encoding a fusion protein, the DNA construct comprising: a first DNA segment encoding a polypeptide selected from the group consisting of: (a) the amino acid sequence of SEQ ID NO: 2 from residue number 1 (Met) to residue number 15 (Ala); (b) the amino acid sequence of SEQ ID NO: 2 from residue number 16 (Arg) to residue number 37 (Ser); (c) the amino acid sequence of SEQ ID NO: 2 from residue number 38 (Leu) to residue number 126 (Ala); (d) the amino acid sequence of SEQ ID NO: 2 from residue number 127 (Pro) to residue number 219 (Gln); and (e) the amino acid sequence of SEQ ID NO:2 from residue number 16 (Arg) to residue number 219 (Gln); and at least one other DNA segment encoding an additional polypeptide, wherein the first and other DNA segments are connected in-frame; and encode the fusion protein.

Within another aspect, the present invention provides a fusion protein produced by a method comprising: culturing a host cell into which has been introduced a vector comprising the following operably linked elements: (a) a transcriptional promoter; (b) a DNA construct encoding a fusion protein as disclosed above; and(c) a transcriptional terminator; and recovering the protein encoded by the DNA segment.

Within another aspect, the present invention provides an isolated zsig63 polypeptide comprising a sequence of amino acid residues that is at least 90% identical to an amino acid sequence selected from the group consisting of: (a) the amino acid sequence as shown in SEQ ID NO: 2 from amino acid number 16 (Arg) to amino acid number 37 (Ser); (b) the amino acid sequence as shown in SEQ ID NO: 2 from amino acid number 38 (Leu) to amino acid number 126 (Ala); (c) the amino acid sequence as shown in SEQ ID NO: 2 from amino acid number 127 (Pro) to amino acid number 219 (Gln); (d) the amino acid sequence as shown in SEQ ID NO:2 from amino acid number 16 (Arg) to amino acid number 219 (Gln); and (e) the amino acid sequence as shown in SEQ ID NO:2 from amino acid number 1 (Met) to amino acid number 219 (Gln). In one embodiment, the isolated polypeptide disclosed above comprises a sequence of amino acid residues selected from the group consisting of: (a) the amino acid sequence as shown in SEQ ID NO: 2 from amino acid number 16 (Arg) to amino acid number 37 (Ser); (b) the amino acid sequence as shown in SEQ ID NO: 2 from amino acid number 38 (Leu) to amino acid number 126 (Ala); (c) the amino acid sequence as shown in SEQ ID NO: 2 from amino acid number 127 (Pro) to amino acid number 219 (Gln); (d) the amino acid sequence as shown in SEQ ID NO:2 from amino acid number 16 (Arg) to amino acid number 219 (Gln); and (e) the amino acid sequence as shown in SEQ ID NO:2 from amino acid number 1 (Met) to amino acid number 219 (Gln).

Within another aspect, the present invention provides a method of producing a zsig63 polypeptide comprising: culturing a cell as disclosed above; and isolating the zsig63 polypeptide produced by the cell.

Within another aspect, the present invention provides a method of detecting, in a test sample, the presence of an antagonist of zsig63 protein activity, comprising: transfecting a zsig63-responsive cell, with a reporter gene construct that is responsive to a zsig63-stimulated cellular pathway; and producing a zsig63 polypeptide by the method as disclosed above; and adding the zsig63 polypeptide to the cell, in the presence and absence of a test sample; and comparing levels of response to the zsig63 polypeptide, in the presence and absence of the test sample, by a biological or biochemical assay; and determining from the comparison, the presence of the antagonist of zsig63 activity in the test sample.

Within another aspect, the present invention provides a method of detecting, in a test sample, the presence of an agonist of zsig63 protein activity, comprising: transfecting a zsig63-responsive cell, with a reporter gene construct that is responsive to a zsig63-stimulated cellular pathway; and adding a test sample; and comparing levels of response in the presence and absence of the test sample, by a biological or biochemical assay; and determining from the comparison, the presence of the agonist of zsig63 activity in the test sample.

Within another aspect, the present invention provides a method of producing an antibody to zsig63 polypeptide comprising the following steps in order: inoculating an animal with a polypeptide selected from the group consisting of. (a) a polypeptide consisting of 9 to 204 amino acids, wherein the polypeptide consists of a contiguous sequence of amino acids in SEQ ID NO:2 from amino acid number 16 (Ala) to amino acid number 219 (Gln); and (b) a polypeptide according as disclosed above; (c) a polypeptide comprising amino acid number 16 (Arg) to 37 (Ser) of SEQ ID NO:2; (d) a polypeptide comprising amino acid number 38 (Leu) to 126 (Ala) of SEQ ID NO:2; (e) a polypeptide comprising amino acid number 127 (Pro) to 219 (Gln) of SEQ ID NO:2; (f) a polypeptide comprising amino acid number 16 (Arg) to amino acid number 219 (Gln) of SEQ ID NO:2; (g) a polypeptide comprising amino acid number 1 (Met) to amino acid number 219 (Gln) of SEQ ID NO:2; (h) a polypeptide comprising amino acid number 14 (Phe) to 19 (Arg) of SEQ ID NO:2; (i) a polypeptide comprising amino acid number 16 (Arg) to 21 (Phe) of SEQ ID NO:2; 0) a polypeptide comprising amino acid number 24 (Gly) to 29 (Asp) of SEQ ID NO:2; (k) a polypeptide comprising amino acid number 25 (Glu) to 30 (Asp) of SEQ ID NO:2; (l) a polypeptide comprising amino acid number 187Glu) to 192 (Glu) of SEQ ID NO:2; (m) a polypeptide comprising amino acid number 24 (Gly) to 33 (Pro) of SEQ ID NO:2; (n) a polypeptide comprising amino acid number 17 (Lys) to 33 (Pro) of SEQ ID NO:2; (o) a polypeptide comprising amino acid number 66 (Thr) to 73 (Pro) of SEQ ID NO:2; (p) a polypeptide comprising amino acid number 103 (Pro) to 108 (Gly) of SEQ ID NO:2; (q) a polypeptide comprising amino acid number 190 (Ala) to 197 (Glu) of SEQ ID NO:2; (r) a polypeptide comprising amino acid number 202 (Lys) to 215 (Gly) of SEQ ID NO:2; and (s) a polypeptide comprising amino acid number 190 (Ala) to 215 (Glu) of SEQ ID NO:2; and wherein the polypeptide elicits an immune response in the animal to produce the antibody; and isolating the antibody from the animal.

Within another aspect, the present invention provides an antibody produced by the method as disclosed above, which binds to a zsig63 polypeptide. In one embodiment, the antibody disclosed above the antibody is a monoclonal antibody. Within another aspect, the present invention provides an antibody that binds to a polypeptide as disclosed above.

These and other aspects of the invention will become evident upon reference to the following detailed description of the invention.

DETAILED DESCRIPTION OF THE INVENTION

Prior to setting forth the invention in detail, it may be helpful to the understanding thereof to define the following terms.

The term "affmity tag" is used herein to denote a peptide segment that can be attached to a polypeptide to provide for purification of the polypeptide or provide sites for attachment of the polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204–1210, 1988; available from Eastman Kodak Co., New Haven, Conn.), streptavidin binding peptide, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGAGCTT-3' are 5'-AGCTTgagt-3' and 3'-tcgacTACC-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, $\alpha$-globin, $\beta$-globin, and myoglobin are paralogs of each other The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about IO amino acid residues are commonly referred to as "peptides".

The term "promoter" denotes a portion of a gene containing DNA sequences that provide for the binding of RNA polymerase and initiation of transcription. Promoter sequences are commonly, but not always, found in the 5' non-coding regions of genes.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand-binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to $\pm 10\%$.

All references cited herein are incorporated by reference in their entirety.

The present invention is based in part upon the discovery of a novel DNA sequence that encodes a human polypeptide having structural similarity to proteins of the bacterial adhesin family.

A standard Northern blot tissue distribution of the MRNA corresponding to this novel DNA revealed high expression in salivary gland, and moderate to high expression in thyroid. Such high expression in salivary gland is consistent with the knowledge in the art regarding anti-bacterial polypeptides, such as defensins, i.e., that they are expressed in epithelial tissues, and are highly inducible upon microbial infection.

The novel zsig63 polypeptides of the present invention were initially identified by querying an EST database for proteins homologous to proteins having a secretory signal sequence. These proteins are characterized by an upstream methionine start site and a hydrophobic region of approximately 13 amino acids, followed by a peptide signal peptidase cleavage site. An EST database was queried for novel DNA sequences whose translations would meet these search criteria. An EST was found and its corresponding cDNA was sequenced. The zsig63 nucleotide sequence is believed to encode the entire coding sequence of the predicted protein. Zsig63 may be a novel host-defense polypeptide, immune modulating factor, anti-pathogenic polypeptide, cell-cell signaling molecule, growth factor, cytokine, secreted extracellular matrix associated protein with growth factor hormone activity, or the like, and is a member a novel protein family.

The sequence of the zsig63 polypeptide was obtained from a single clone believed to contain its corresponding polynucleotide sequence. The clone was obtained from a salivary gland library. Other libraries that might also be searched for such sequences include thyroid, prostate, and the like.

The nucleotide sequence of a representative zsig63-encoding DNA is described in SEQ ID NO:1 (from nucleotide 128 to 784), and its deduced 219 amino acid sequence is described in SEQ ID NO:2. In its entirety, the zsig63 polypeptide (SEQ ID NO:2) represents a fill-length polypeptide segment (residue 1 (Met) to residue 219 (Gln) of SEQ ID NO:2). The domains and structural features of the zsig63 polypeptide are further described below.

Analysis of the zsig63 polypeptide encoded by the DNA sequence of SEQ ID NO:1 revealed an open reading frame encoding 219 amino acids (SEQ ID NO:2) comprising a predicted secretory signal peptide of 15 amino acid residues (residue 1 (Met) to residue 15 (Ala) of SEQ ID NO:2), and a mature polypeptide of 204 amino acids (residue 16 (Arg) to residue 219 (Gln) of SEQ ID NO:2). Structural analysis revealed the following 3 structural domains:

(1) The first domain, referred to hereinafter as "domain 1," corresponds approximately to amino acid residues 16 (Arg) to amino acid residue 37 (Ser) of SEQ ID NO:2. Domain 1 contains an acid region of 5 acid residues (corresponding to amino acid residues 25 (Glu) to amino acid residue 30 (Asp) of SEQ ID NO:2).

(2) The second domain, referred to hereinafter as "domain 2," corresponds approximately to amino acid residues 38 (Leu) to amino acid residue 126 (Ala) of SEQ ID NO:2. Domain 2 contains a high concentration of Tyrosine residues (16% over 49 amino acids). Tyrosine residues in domain 2 are present, in reference to SEQ ID NO:2 at the following positions: 42, 52, 53, 62, 67, 75, 86, and 88.

(3) The third domain, referred to hereinafter as "domain 3," corresponds approximately to amino acid residues 127 (Pro) to amino acid residue 219 (Gln) of SEQ ID NO:2. Domain 3 contains a region rich in coil-like structure (corresponding to amino acid residues 127 (Pro) to amino acid residue 208 (Pro) of SEQ ID NO:2) that contains 16 full evenly-spaced coil-like repeats punctuated by proline residues every 5 amino acids. These repeats are defined as follows, based on the proline residues and corresponding reference to SEQ ID NO:2:

"repeat 1" corresponding to amino acid residues 124 (Ile) to amino acid residue 133 (Pro) of SEQ ID NO:2;

"repeat 2" corresponding to amino acid residues 134 (Ala) to amino acid residue 138 (Pro) of SEQ ID NO:2;

"repeat 3" corresponding to amino acid residues 139 (Leu) to amino acid residue 143 (Pro) of SEQ ID NO:2;

"repeat 4" corresponding to amino acid residues 144 (Val) to amino acid residue 148 (Pro) of SEQ ID NO:2;

"repeat 5" corresponding to amino acid residues 149 (Ala) to amino acid residue 153 (Pro) of SEQ ID NO:2;

"repeat 6" corresponding to amino acid residues 154 (Val) to amino acid residue 158 (Pro) of SEQ ID NO:2.

"repeat 7" corresponding to amino acid residues 159 (Ala) to amino acid residue 163 (Pro) of SEQ ID NO:2;

"repeat 8" corresponding to amino acid residues 164 (Val) to amino acid residue 168 (Pro) of SEQ ID NO:2;

"repeat 9" corresponding to amino acid residues 169 (Ala) to amino acid residue 173 (Pro) of SEQ ID NO:2;

"repeat 10" corresponding to amino acid residues 174 (Val) to amino acid residue 178 (Pro) of SEQ ID NO:2;

"repeat 11" corresponding to amino acid residues 179 (Ala) to amino acid residue 183 (Pro) of SEQ ID NO:2;

"repeat 12" corresponding to amino acid residues 184 (Val) to amino acid residue 188 (Pro) of SEQ ID NO:2.

"repeat 13" corresponding to amino acid residues 189 (Ala) to amino acid residue 193 (Pro) of SEQ ID NO:2;

"repeat 14" corresponding to amino acid residues 194 (Ser) to amino acid residue 198 (Pro) of SEQ ID NO:2;

"repeat 15" corresponding to amino acid residues 199 (Ala) to amino acid residue 203 (Pro) of SEQ ID NO:2; and "repeat 16" corresponding to amino acid residues 204 (Ala) to amino acid residue 208 (Pro) of SEQ ID NO:2.

Structural modeling is performed by one of skill in the art, using modelling software, such as InsightII® (Biosym/MSI, San Diego, Calif.). The presence of low variance and structural motifs generally correlate with or define important structural regions in proteins. Regions of low variance (e.g., hydrophobic clusters) are generally present in regions of structural importance (Sheppard, P. et al., supra.). Such regions of low variance often contain rare or infrequent amino acids, such as Tryptophan. The regions flanking and between such conserved and low variance motifs may be more variable, but are often functionally significant because they may relate to or define important structures and activities such as binding domains, biological and enzymatic activity, signal transduction, cell-cell interaction, tissue localization domains and the like.

The coil-like repeats in domain 3 of zsig63 polypeptide can be used as a tool to identify new family members. For instance, reverse transcription-polymerase chain reaction (RT-PCR) can be used to amplify sequences encoding the conserved motif from RNA obtained from a variety of tissue sources. More specifically, degenerate DNA probes and degenerate primers can be employed to identify other human or zsig63-like polynucleotides. In particular, highly degenerate primers designed from the above sequences are useful for this purpose.

SEQ ID NO:3 is a degenerate polynucleotide sequence that encompasses all polynucleotides that encode the zsig63 polypeptide of SEQ ID NO:2. Thus, zsig63 polypeptide-encoding polynucleotides ranging from nucleotide 1 to nucleotide 657 of SEQ ID NO:3 are contemplated by the present invention. Also contemplated by the present invention are fragments and fusions as described above with respect to SEQ ID NO:1 and which are formed from analogous regions of SEQ ID NO:3. The symbols in SEQ ID NO:3 are summarized in Table 1 below.

TABLE 1

| Nucleotide | Resolutions | Complement | Resolutions |
| --- | --- | --- | --- |
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | A\|T |
| W | A\|T | W | C\|G |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

TABLE 2

| Amino Acid | Letter | Codons | Degenerate Codon |
| --- | --- | --- | --- |
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X | — | NNN |
| Gap |  | — — |  |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., Nuc. Acids Res. 8:1893–912, 1980; Haas, et al. Curr. Biol. 6:315–24, 1996; Wain-Hobson, et al., Gene 13:355–64, 1981; Grosjean and Fiers, Gene 18:199–209, 1982; Holm, Nuc. Acids Res. 14:3075–87, 1986; Ikemura, J. Mol. Biol. 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premnier 4.0™ (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40–50% formamide, up to about 6×SSC, about 5×Denhardt's solution, zero up to about 10% dextran sulfate, and about 10–20 µg/ml denatured commercially-available carrier DNA. Generally, such stringent conditions include temperatures of 20–70° C. and a hybridization buffer containing up to 6×SSC and 0–50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for isolating DNA and RNA are well known in the art. It is generally preferred to isolate RNA from bronchial epithelium, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. Polynucleotides encoding zsig63 polypeptides are then identified and isolated by, for example, hybridization or PCR.

The present invention further provides counterpart polypeptides and polynucleotides from other species (orthologs). These species include, but are not limited to mammalian, avian, amphibian, reptile, fish, insect and other vertebrate and invertebrate species. Of particular interest are zsig63 polypeptides from other mammalian species, including murine, rat, porcine, ovine, bovine, canine, feline, equine and other primate proteins. Species homologs of the human proteins can be cloned using information and compositions provided by the present invention in combination with conventional cloning techniques. For example, a cDNA can be cloned using MRNA obtained from a tissue or cell type that expresses the protein. Suitable sources of mRNA can be identified by probing Northern blots with probes designed from the sequences disclosed herein. A library is then prepared from mRNA of a positive tissue of cell line. A zsig63 polypeptide-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to zsig63 polypeptide. Similar techniques can also be applied to the isolation of genomic clones.

Those skilled in the art will recognize that the sequences disclosed in SEQ ID NO:1 and SEQ ID NO:2 represent a single allele of the human zsig63 gene and polypeptide, and that allelic variation and alternative splicing are expected to occur. Allelic variants can be cloned by probing cDNA or genomic libraries from different individuals according to standard procedures. Allelic variants of the DNA sequence shown in SEQ ID NO:2 including those containing silent mutations and those in which mutations result in amino acid sequence changes, are within the scope of the present invention.

The present invention also provides isolated zsig63 polypeptides that are substantially similar to the polypeptides of SEQ ID NO:2 and their orthologs. The term "substantially similar" is used herein to denote polypeptides having 60%, preferably 70% and more preferably at least 80%, sequence identity to the sequences shown in SEQ ID NO:2 or their orthologs or paralogs. Such polypeptides will more preferably be at least 90% identical, and most preferably 95% or more identical to SEQ ID NO:2 or its orthologs or paralogs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

Total number of identical matches/[length of the longer sequence plus the number of gaps introduced into the longer sequence in order to align the two sequences]×100

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zsig63. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifing regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then restored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J MoL Biol.* 48:444 (1970); Sellers, *SIAM J Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The BLOSUM62 table (Table 3) is an amino acid substitution matrix derived from about 2,000 local multiple alignments of protein sequence segments, representing highly conserved regions of more than 500 groups of related proteins (Henikoff and Henikoff, *Proc. Nat'l Acad Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), thioredoxin, ubiquitin, cellulose binding protein, T7 polymerase, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.; New England Biolabs,

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Beverly, Mass.). The present invention thus includes polypeptides of from about 170 to about 250 amino acid residues that comprise a sequence that is at least 80%, preferably at least 90%, and more preferably 95% or more identical to the corresponding region of SEQ ID NO:2. Polypeptides comprising affinity tags can further comprise a proteolytic cleavage site between the zsig63 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethyl-cysteine, hydroxyethylhomocysteine, nitroglutamine, homoglutamine, pipecolic acid, tertleucine, norvaline, 2-azaphenylalanine, 3-azaphenylalanine, 4-azaphenylalanine, 4-fluorophenylalanine, 4-hydroxyproline, 6-N-methyl lysine, 2-aminoisobutyric acid, isovaline and a-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Meth. Enzymol. 202:301, 1991; Chung et al., Science 259:806–09, 1993; and Chung et al., Proc. Natl. Acad. Sci. USA 90:10145–49, 1993). In a second method, translation is carried out in Xenopus oocytes by mictoinjection of mutated mRNA and chemically aminoacylated suppressor tRNAs (Turcatti et al., J. Biol. Chem. 271:19991–98, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470–76, 1994.

Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395–403, 1993).

A limited number of non-conservative amino acids, amino acids that are not encoded by the genetic code, non-naturally occurring amino acids, and unnatural amino acids may be substituted for zsig63 polypeptide amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the zsig63 polypeptides of the present invention can be identified according to procedures known in the art, such as site-directed mutagenesis or alanine-scanning mutagenesis (Cunningham and Wells, Science 244: 1081–1085, 1989). In the latter technique, single alanine mutations are introduced at every residue in the molecule, and the resultant mutant molecules are tested for biological activity (e.g., anti-microbial activity) to identify amino acid residues that are critical to the activity of the molecule. See also, Hilton et al., J. Biol. Chem. 271:4699–4708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–312, 1992; Smith et al., J. Mol. Biol. 224:899–904, 1992; Wlodaver et al., FEBS Lett. 309:59–64, 1992. The identities of essential amino acids can also be inferred from analysis of homologies with related β-defensins.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, Current Opin. Struct. Biol. 5:372–376, 1995 and Cordes et al., Current Opin. Struct. Biol. 6:3–10, 1996). In general, when designing modifications to molecules or identifying specific fragments determination of structure will be accompanied by evaluating activity of modified molecules.

Amino acid sequence changes are made in zsig63 polypeptides so as to minimize disruption of higher order structure essential to biological activity. For example, when the zsig63 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., Nat. Struct. Biol. 2:266–268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). It is generally believed that if a modified molecule does not have the same disulfide bonding pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205–214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961–964, 1992).

A Hopp/Woods hydrophilicity profile of the zsig63 protein sequence as shown in SEQ ID NO:2 can be generated (Hopp et al., *Proc. Natl. Acad. Sci.* 78:3824–3828, 1981; Hopp, *J. Immun. Meth.* 88:1–18, 1986 and Triquier et al., *Protein Engineering* 11: 153–169, 1998). The profile is based on a sliding six-residue window. Buried G, S, and T residues and exposed H, Y, and W residues were ignored. For example, in zsig63, hydrophilic regions include amino acid residues 14 (Phe) to 19 (Arg) of SEQ ID NO: 2, amino acid residues 16 (Arg) to 21 (Phe) of SEQ ID NO: 2, amino acid residues 24 (Gly) to 29 (Asp) of SEQ ID NO: 2, amino acid residues 25 (Glu) to 30 (Asp) of SEQ ID NO: 2, and amino acid residues 187Glu) to 192 (Glu) of SEQ ID NO: 2.

Those skilled in the art will recognize that hydrophilicity or hydrophobicity will be taken into account when designing modifications in the amino acid sequence of a zsig63 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO: 2., and described above.

The identities of essential amino acids can also be inferred from analysis of sequence similarity between other known zsig63 protein family members with zsig63. Using methods such as "FASTA" analysis described previously, regions of high similarity are identified within a family of proteins and used to analyze amino acid sequence for conserved regions. An alternative approach to identifing a variant zsig63 polynucleotide on the basis of structure is to determine whether a nucleic acid molecule encoding a potential variant zsig63 polynucleotide can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl Acad. Sci. USA* 88:4498 (1991), Coombs and Corey, "Site-Directed Mutagenesis and Protein Engineering," in *Proteins: Analysis and Design*, Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J Biol. Chem.* 271:4699 (1996).

The present invention also includes functional fragments of zsig63 polypeptides and nucleic acid molecules encoding such functional fragments. A "functional" zsig63 or fragment thereof defined herein is characterized by its proliferative or differentiating activity, by its ability to induce or inhibit specialized cell functions, or by its ability to bind specifically to an anti- zsig63antibody or zsig63 receptor (either soluble or immobilized).

Routine deletion analyses of nucleic acid molecules can be performed to obtain functional fragments of a nucleic acid molecule that encodes a zsig63 polypeptide. As an illustration, DNA molecules having the nucleotide sequence of SEQ ID NO: 1 or fragments thereof, can be digested with Bal31 nuclease to obtain a series of nested deletions. These DNA fragments are then inserted into expression vectors in proper reading frame, and the expressed polypeptides are isolated and tested for zsig63 activity, or for the ability to bind anti-zsig63 antibodies or zsig63 receptor. One alternative to exonuclease digestion is to use oligonucleotide-directed mutagenesis to introduce deletions or stop codons to specify production of a desired zsig63 fragment. Alternatively, particular fragments of a zsig63 polynucleotide can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987); Herschman, "The EGF Receptor," in *Control of Animal Cell Proliferation* 1, Boynton et al., (eds.) pages 169–199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zsig63 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., anti-microbial activity) can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly other cytokines, to provide multi-functional molecules. For example, one or more helices from zsig63 can be joined to other cytokines to enhance their biological properties or efficiency of production.

The present invention thus provides a series of novel, hybrid molecules in which a segment comprising one or more of the domains, coil-like structure, or repeats, of zsig63 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Using the methods discussed above, one of ordinary skill in the art can identify and/or prepare a variety of polypeptides that are substantially similar to residues 16 to 219 of SEQ ID NO:2 or allelic variants thereof and retain the anti-microbial properties of the wild-type protein. Such polypeptides may include additional amino acids from affinity tags and the like; Such polypeptides may also include additional polypeptide segments as generally disclosed above.

The polypeptides of the present invention, including full-length proteins, fragments thereof and fusion proteins, can be produced in genetically engineered host cells according to conventional techniques. However, host cells must be selected with some care as a result of the anti-microbial activity of the molecules of the present invention. For example, any cell culture-based system must be evaluated, because zsig63 polypeptides, fragments, fusion proteins, antibodies, agonists or antagonists may kill the host cell as a part of an anti-microbial function. Zsig63 polypeptides are of a small enough size to permit preparation by PCR or other protein chemistry techniques to avoid any potential host cell toxicity problems. Alternatively, native or engineered precursor proteins, prior to post-translational cleavage to yield the mature zsig63 polypeptide, are inactive, thereby limiting host cell cytotoxicity prior to lysosomal packaging. See, for example, Lehrer et al., Cell 64: 229–30, 1991. Thus, precursor proteins to zsig63 polypeptides may be produced in microbial cell culture.

Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al. (eds.), *Current Protocols in Molecular Biology*, John Wiley and Sons, Inc., N.Y., 1987.

In general, a DNA sequence encoding a zsig63 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig63 polypeptide into the secretory pathway of a host cell, a secretory signal sequence (also known as a leader sequence, prepro sequence or pre sequence) is provided in the expression vector. The secretory signal sequence may be that of the zsig63 polypeptide, disclosed herein, or may be derived from another secreted protein (e.g., t-PA) or synthesized de novo. The secretory signal sequence is joined to the zsig63 polypeptide-encoding DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1 (Met) through 15 (Ala) of SEQ ID NO:2, is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current*

*Protocols in Molecular Biology*, John Wiley and Sons, Inc., N.Y., 1987), liposome-mediated transfection (Hawley-Nelson et al., *Focus* 15:73, 1993; Ciccarone et al., *Focus* 15 15:80, 1993), and viral vectors (A. Miller and G. Rosman, *Bio Techniques* 7:980–90, 1989; Q. Wang and M. Finer, *Nature Med.* 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the zsig63 polypeptide is inserted into the baculoviral genome in place of the AcNPV polyhedrin gene coding sequence by one of two methods. The first is the traditional method of homologous DNA recombination between wild-type AcNPV and a transfer vector containing the zsig63 flanked by AcNPV sequences. Suitable insect cells, e.g. SF9 cells, are infected with wild-type AcNPV and transfected with a transfer vector comprising a zsig63 polynucleotide operably linked to an AcNPV polyhedrin gene promoter, terminator, and flanking sequences. See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. Natural recombination within an insect cell will result in a recombinant baculovirus which contains zsig63 driven by the polyhedrin promoter. Recombinant viral stocks are made by methods commonly used in the art.

The second method of making recombinant baculovirus utilizes a transposon-based system described by Luckow (Luckow et al., *J Virol.* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zsig63 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zsig63. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkin and Possee, *J. Gen. Virol.* 71:971–6, 1990; Bonning. et al., *J. Gen. Virol.* 75:1551–6, 1994; and, Chazenbalk and Rapoport, *J. Biol. Chem.* 270:1543–9, 1995. In such transfer vector constructs, a short or long version of the basic protein promoter can be used. Moreover, transfer vectors can be constructed which replace the native zsig63 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zsig63 secretory signal sequence. In addition, transfer vectors can include an in-frame fusion with DNA encoding an epitope tag at the C- or N-terminus of the expressed zsig63 polypeptide, for example, a Glu-Glu epitope tag (Grusserneyer et al., *Proc. Natl. Acad. Sci.* 82:7952–4, 1985). Using a technique known in the art, a transfer vector containing zsig63 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. *Sf*9 cells. Recombinant virus that expresses zsig63 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kan.) or Express FiveO™ (Life Technologies) for the *T ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. The recombinant virus-infected cells typically produce the recombinant zsig63 polypeptide at 12–72 hours post-infection and secrete it with varying efficiency into the medium. The culture is usually harvested 48 hours post-infection. Centrifugation is used to separate the cells from the medium (supernatant). The supernatant containing the zsig63 polypeptide is filtered through micropore filters, usually 0.45 pm pore size. Procedures used are generally described in available laboratory manuals (King and Possee, ibid.; O'Reilly et al., ibid.; Richardson, ibid.). Subsequent purification of the zsig63 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strais of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zsig63 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant zsig63 polypeptides (or chimeric zsig63 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharnacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Phanmacia LKB Biotechnology, Uppsala, Sweden, 1988.

The polypeptides of the present invention can be isolated by exploitation of their structural and biological properties. For example, immobilized metal ion adsorption (IMAC) chromatography can be used to purif histidine-rich proteins or proteins having a His-affinity tag. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinty tag (e.g., maltose-binding protein, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

zsig63 polypeptides or fragments thereof may also be prepared through chemical synthesis. zsig63 polypeptides may be monomers or multimers; glycosylated or nonglycosylated; pegylated or non-pegylated; amidated or non amidated; sulfated or non-sulfated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem.* 34:595, 1970. After the entire synthesis of the desired peptide on a solid support, the peptide-resin is washed with a reagent which cleaves the polypeptide from the resin and removes most of the side-chain protecting groups. Such methods are well established in the art.

Molecules of the present invention can be used to identify and isolate receptors that bind zsig63 polypeptide. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (Methods in Enzymol., vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

An assay system that uses a ligand-binding receptor (or an antibody, one member of a complement/ anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/ anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/ tissue-specific delivery of generic anti-complementary-detectable/ cytotoxic molecule conjugates.

In another embodiment, zsig63-cytokine fusion proteins or antibody-cytokine fusion proteins can be used for enhancing in vivo killing of target tissues (for example, blood and bone marrow cancers), if the zsig63 polypeptide or anti-zsig63 antibody targets the hyperproliferative blood or bone marrow cell (See, generally, Hornick et al., *Blood* 89:4437–47, 1997). Hornick et al. described fusion proteins that target a cytokine to a desired site of action, thereby providing an elevated local concentration of cytokine. Suitable zsig63 polypeptides or anti-zsig63 antibodies can target an undesirable cell or tissue (i.e., a tumor or a leukemia), and the fused cytokine can mediate improved target cell lysis by effector cells. Suitable cytokines for this purpose include interleukin 2 and granulocyte-macrophage colony-stimulating factor (GM-CSF), for instance.

In yet another embodiment, if the zsig63 polypeptide or anti-zsig63 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Another aspect of the present invention includes zsig63 polypeptide fragments. Preferred fragments include the leader sequence, ranging from amino acid 1 (Met) to amino acid 15 (Ala) of SEQ ID NO:2. Such leader sequences may be used to direct the secretion of other polypeptides. Such fragments of the present invention may be used as follows: the alternative secretion leader fragments are formed as fusion proteins with alternative proteins selected for secretion; plasmids bearing regulatory regions capable of directing the expression of the fusion protein are introduced into test cells; and secretion of the protein is monitored.

Moreover, using methods described in the art, polypeptide fusions, or hybrid zsig63 proteins, are constructed using regions or domains of zsig63 in combination with those of paralogs, orthologs, or heterologous proteins (Sambrook et al., ibid., Altschul et al., ibid., Picard. D., *Cur. Opin. Biology*, 5:511–515, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion polypeptides can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between zsig63 of the present invention with the functionally equivalent domain(s) from another family member. Such domains include, but are not limited to the secretory signal sequence, and domains 1 through 3, and the coil-like structure, described herein. Such fusion proteins would be expected to have a biological functional profile that is the same or similar to polypeptides of the present invention or other known family proteins or to a heterologous protein, depending on the fusion constructed. Moreover, such fusion proteins may exhibit other properties as disclosed herein.

Standard molecular biological and cloning techniques can be used to swap the equivalent domains between the zsig63 polypeptide and those polypeptides to which they are fused. Generally, a DNA segment that encodes a domain of interest, e.g., a zsig63 domain 1, 2, or 3, or a motif described herein, is operably linked in frame to at least one other DNA segment encoding an additional polypeptide and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a mature polypeptide; or a DNA construct would encode from N-terminus to C-terminus a fusion protein comprising a signal polypeptide followed by domain-1, followed by domain-2, followed by domain-3, or as interchanged with equivalent regions from another protein. Such fusion proteins can be expressed, isolated, and assayed for activity as described herein. Polypeptide linkers are preferably employed if necessary to provide separation of component polypeptides of the fusion or to allow for flexibility of the fusion protein, thereby preserving the anti-microbial activity of each defensin component of the fusion protein. Those of ordinary skill in the art are capable of designing such linkers.

Within another aspect of the present invention there is provided a -pharmaceutical composition comprising purified zsig63 polypeptide in combination with a pharmaceutically acceptable vehicle. Such pharmaceutical compositions are used in the treatment of conditions associated with pathological microbes, including bacterial, fungal and viral infections. Antibacterial applications of zsig63 polypeptide include situations where the pathogen has become resistant to standard treatments. For example, hospital sepsis is an increasing problem, since Staphylococcus and other bacterial and microbial strains have become resistant to commonly used antibiotics.

In general, anti-microbial activity of zsig63 polypeptides, fragments, fusions, antibodies, agonists and antagonists can be evaluated by techniques that are known in the art. More specifically, anti-microbial activity can be assayed by evaluating the sensitivity of microbial cell cultures to test agents and by evaluating the protective effect of test agents on infected mice. See, for example, Musiek et al., *Antimicrob. Agents Chemothr.* 3: 40, 1973. Antiviral activity can also be assessed by protection of mammalian cell cultures. Known techniques for evaluating anti-microbial activity include, for example, Barsum et al., *Eur. Respir. J.* 8(5): 709–14, 1995; Sandovsky-Losica et al., *J. Med. Vet. Mycol* (England) 28(4): 279–87, 1990; Mehentee et al., *J. Gen. Microbiol* (England) 135 (Pt. 8): 2181–8, 1989; Segal and Savage, *Journal of Medical and Veterinary Mycology* 24: 477–479, 1986 and the like. Known assays specific for anti-viral activity include, for example, those described by Daher et al., *J. Virol.* 60(3): 1068–74, 1986.

In addition, contract laboratories offer services in evaluating antimicrobial properties. For example, Panlabs, Inc. of Bothell, Washington offer in vitro or in vivo testing for bacteria, gram negative (*Enterobacter cloacae, Escherichia* coli, *Klebsiella pneumonia, Proteus vulgaris, Pseudomonas aeruginosa, Salmonella typhimurium* and *Serratia marcescens*), gram positive (*Bacillus subtilis, Brevebacterium ammoniagenes, Corynebacterium minutissimum, Micrococcus luteus, Mycobacterium ranae*, Staphylococcus strains and Streptococcus strains) and anaerobic organisms (*Actinomyces viscosus, Bacteroides fragilis, Clostridium sporogenes, Corynebacterium acnes, Helicobacter pylori* and *Porphyromonas gingivalis*), as well as for protozoa (*Trichomonas foetus*) and fingi (e.g., *Candida albicans, Epidermophyton floccosum, Exophiala jeanselmei*, Microsporum strains, Trichophyton strains and the like). Also, Molecular Probes of Oregon has commercially available fluorescence technology for use in bacteriology.

If desired, zsig63 polypeptide, fragment, fusion protein, agonist, antagonist or antibody performance in this regard can be compared to proteins known to be fumctional in this regard, such as proline-rich proteins, lysozyme, histatins, lactoperoxidase or the like. In addition, zsig63 polypeptide, fragment, fusion protein, antibody, agonist or antagonist may be evaluated in combination with one or more anti-microbial agents to identify synergistic effects.

High expression of zsig63 in salivary gland suggests that anti-microbial polypeptides of the present invention can be used for treatment of dental carries (tooth decay), periodontal disease, thrush, and gastrointestinal disease. Other applications can be used in urinary tract infections, vaginal infections, prevention of infection in skin and other epithelial wounds. As such, the polypeptides of the present invention can help establish normal microflora and protect against pathogenic colonization and invasion.

Moreover, microorganisms have specific infective stages where they decorate their surface with proline coil containing proteins. One theory is that they are decoying or evading the host immune system by expressing host-like, but inactive, proteins on their surfaces. The zsig63 polypeptide of the present invention can be one of these host polypeptides that the microorganism is mimicking. Moreover, there may be a correlation with Zinc and resistance to microbial infection. If zsig63 binds zinc (or some other cation) there may be a delivery fumction, or immune activation function with zinc as a co-factor for regulation of specific cell types, or defensive enzymes. Such immune activation by zsig63 polypeptides can be assessed by assays that are well known in the art.

The pharmaceutical compositions of the present invention may also be used when pro-inflammatory activity is desired. Applications for such pro-inflammatory activity include the treatment of chronic tissue damage, particularly in areas having a limited or damaged vascular system, e.g., damage in extremities associated with diabetes. In contrast, antagonists to zsig63 polypeptides may be useful as anti-inflammatory agents.

Zsig63 polypeptide pharmaceutical compositions of the present invention may also be used in the treatment of conditions where stimulation of immune responsiveness is desired. Such conditions include the treatment of patients having incompetent immune systems, such as AIDS patients or individuals that have undergone chemotherapy, radiation treatment or the like.

Because zsig63 polypeptide was found in a salivary gland library and cystic fibrosis is characterized by frequent microbial infection, pharmaceutical compositions containing zsig63 polypeptide are also contemplated for use in the treatment of lung infections associated with cystic fibrosis. Also contemplated by the present invention are engineered zsig63 polypeptides that are characterized by decreased sensitivity to salt concentration. Decreased sensitivity to high salt concentration will preserve anti-microbial activity of engineered zsig63 polypeptides in high salt environments, such as in the lung airways of patients suffering from cystic fibrosis. In this manner, pharmaceutical compositions containing engineered zsig63 polypeptides that are formulated for delivery to the lungs can be used to treat lung infections associated with cystic fibrosis.

Another aspect of the present invention involves the detection of zsig63 polypeptides in cell culture or in a serum sample or tissue biopsy of a patient undergoing evaluation for SPG, Chediak-Higashi syndrome, or other conditions characterized by an alteration in defensin concentration. Zsig63 polypeptides can be detected using immunoassay techniques and antibodies capable of recognizing a zsig63 polypeptide epitope, as described herein. More specifically, the present invention contemplates methods for detecting zsig63 polypeptide comprising:

exposing a solution or sample or cell culture lysate or supernatant, possibly containing zsig63 polypeptide, to an antibody attached to a solid support, wherein said antibody binds to a first epitope of a zsig63 polypeptide;

washing said immobilized antibody-polypeptide to remove unbound contaminants;

exposing the immobilized antibody-polypeptide to a second antibody directed to a second epitope of a zsig63 polypeptide, wherein the second antibody is associated with a detectable label; and detecting the detectable label. Zsig63 polypeptide concentration differing from that of controls may be indicative of SPG, Chediak-Higashi syndrome or other conditions characterized by an alteration in defensin concentration. In addition, expression of zsig63 may be monitored in cystic fibrosis patients as a predictor of the onset of infectious crises. Also, high defensin levels have been associated with cytotoxic effects in lung, indicating that other host anti-microbial polypeptides, such as zsig63 polypeptide levels can be used as indicators for disease onset and cytotoxicity, and used to direct treatment for averting or addressing such cytotoxicity. For example, antibodies directed to zsig63 polypeptide can be administered to inactivate the same in a treatment modality.

Within additional aspects of the invention there are provided antibodies or synthesized binding proteins(e.g., those generated by phage display, *E. coli* Fab, and the like) that specifically bind to the zsig63 polypeptides described above. Such antibodies are useful for, among other uses as described herein, preparation of anti-idiotypic antibodies. Synthesized binding proteins may be produced by phage display using commercially available kits, such as the Ph.D.™ Phage Display Peptide Library Kits available from New England Biolabs, Inc. (Beverly, Mass.). Phage display techniques are described, for example, in U.S. Pat. Nos. 5,223,409, 5,403,484 and 5,571,698.

An additional aspect of the present invention provides methods for identifying agonists or antagonists of the zsig63 polypeptides disclosed above, which agonists or antagonists may have valuable properties as discussed further herein. Within one embodiment, there is provided a method of identifying zsig63 polypeptide agonists, comprising providing cells responsive thereto, culturing the cells in the presence of a test compound and comparing the cellular response with the cell cultured in the presence of the zsig63 polypeptide, and selecting the test compounds for which the cellular response is of the same type.

Within another embodiment, there is provided a method of identifying antagonists of zsig63 polypeptide, comprising providing cells responsive to a zsig63 polypeptide, culturing a first portion of the cells in the presence of zsig63 polypeptide, culturing a second portion of the cells in the presence of the zsig63 polypeptide and a test compound, and detecting a decrease in a cellular response of the second portion of the cells as compared to the first portion of the cells.

A further aspect of the invention provides a method of studying chemoattraction of monocytes in cell culture, comprising incubating monocytes in a culture medium comprising a zsig63 polypeptide, fragment, fusion protein, antibody, agonist or antagonist to study or evaluate monocyte chemoattraction. Such evaluation may be conducted using methods known in the art, such as those described by Territo et al. referenced above.

Melanocortin receptors are G-coupled protein receptors which activate adenylate cyclase and cause calcium flux. The agouti protein (which contains a 36 amino acid domain that is toxin-like) is thought to inhibit the binding of MSH-alpha to MC1 and MC4. In addition, the agouti protein is thought to be an antagonist of calcium channels, and certain toxins are believed to modulate ion flux. Experimental evidence has been generated, suggesting that defensins are capable of blocking calcium channels. Similarly, zsig63 polypeptides could have such properties.

A further aspect of the invention provides a method of studying activity of the melanocortin family of receptors in cell culture, comprising incubating cells that endogenously bear such receptors (e.g., ACTH receptors or the like) or cells that have been engineered to bear such receptors in a culture medium comprising a ligand or putative ligand and zsig63 polypeptide, fragment, fusion protein, antibody, agonist or antagonist to study or evaluate ligand or putative ligand binding and/or ion flux regulation or modulation. Such evaluation may be conducted using methods known in the art, such as those described by Zhu et al. referenced above.

A further aspect of the invention provides a method of studying ion flux in cell culture, comprising incubating cells that are capable of ion flux, such as calcium flux, sodium flux, potassium flux or the like, in a culture medium comprising zsig63 polypeptide, fragment, fusion protein, antibody, agonist or antagonist to study or evaluate ion flux regulation or modulation.

A further aspect of the invention provides a method of studying cytocidal activity against mammalian cells, such as tumor cells, in cell culture, comprising incubating such cells in a culture medium comprising a zsig63 polypeptide, fragment, fusion protein, antibody, agonist or antagonist at high test agent and low cell concentration to study or evaluate cytocidal activity. Such evaluation may be conducted using methods known in the art, such as those described by Lichtenstein et al., *Blood* 68: 1407–10, 1986 and Sheu et al., *Antimicrob. Agents Chemother.* 28: 626–9, 1993.

Another aspect of the present invention involves the use of zsig63 polypeptides, fragments, fusion proteins or agonists as cell culture reagents in in vitro studies of exogenous microorganism infection, such as bacterial, viral or fungal infection. Such moieties may also be used in in vivo animal models of infection.

An additional aspect of the present invention is to study epithelial cell defensin induction in cell culture. In this aspect of the present invention, epithelial cells are cultured and exposed to pathogenic stimuli. Induction of zsig63 polypeptide production by the epithelial cells is then measured.

A high level of expression of zsig63 polypeptide was observed by Northern blot in the trachea and by dot blot in the salivary gland and trachea. Consequently, another aspect of the present invention involves the detection of zsig63 polypeptides in the serum or tissue biopsy of a patient undergoing evaluation for salivary gland function or dysfunction. Such zsig63 polypeptides can be detected using immunoassay techniques and antibodies capable of recognizing zsig63 polypeptide epitopes.

More specifically, the present invention contemplates methods for detecting zsig63 polypeptide comprising:

exposing a solution possibly containing zsig63 polypeptide to an antibody attached to a solid support, wherein said antibody binds to a first epitope of a zsig63 polypeptide;

washing said immobilized antibody-polypeptide to remove unbound contaminants;

exposing the immobilized antibody-polypeptide to a second antibody directed to a second epitope of a zsig63 polypeptide, wherein the second antibody is associated with a detectable label; and detecting the detectable label. Changes in serum or biopsy zsig63 polypeptide concentration (relative to normal serum or tissue concentration) may be indicative of dysfunction of the salivary gland.

Salivary gland dysfunction includes digestive dysfunction, wound healing dysfunction, inadequate saliva production or composition, mucosal integrity breakdown, and failure of or diminished anti-microbial function. Detection of zsig63 polypeptide at relatively high levels in the trachea may indicate that such polypeptides may serve as a marker of lung dysfunction. Moreover, zsig63 expression is detected in lung. Examples of conditions associated with salivary gland or lung dysfunction include salivary gland carcinoma, sarcoidosis, pneumocystic carinii (particularly as associated with AIDS patients), emphysema, chronic bronchitis, cystic fibrosis, ARDS, SIDS or the like. In addition, zsig63 polypeptides are expressed in the prostate at a level similar to trachea, as well as in the salivary gland. The prostate gland is androgen regulated and shares other properties with salivary glands. Consequently, dysfunction thereof, such as prostate adenocarcinoma or the like, may also be detected using zsig63 polypeptides or zsig63 antibodies.

Also, the salivary glands synthesize and secrete a number of proteins having diverse biological functions. Such proteins facilitate lubrication of the oral cavity (e.g., mucins and proline-rich proteins), rernineralization (e.g., statherin and ionic proline-rich proteins) and digestion (e.g., amylase, lipase and proteases) and provide anti-microbial (e.g., proline-rich proteins, lysozyme, histatins and lactoperoxidase) and mucosal integrity maintenance (e.g., mucins) capabilities. In addition, saliva is a rich source of growth factors synthesized by the salivary glands. For example, saliva is known to contain epidermal growth factor (EGF), nerve growth factor (NGF), transforming growth factor-alpha (TGF-α), transforming growth factor-beta (TGF-β), insulin, insulin-like growth factors I and II (IGF-I and IGF-II) and fibroblast growth factor (FGF). See, for example, Zelles et al., *J. Dental. Res.* 74(12): 1826–32, 1995. Synthesis of growth factors by the salivary gland is believed to be androgen-dependent and to be necessary for the health of the oral cavity and gastrointestinal tract.

Thus, zsig63 polypeptides, agonists or antagonists thereof may be therapeutically useful for aiding digestion. To verify the presence of this capability in zsig63 polypeptides, agonists or antagonists of the present invention, such zsig63 polypeptides, agonists or antagonists are evaluated with respect to their ability to break down starch according to procedures known in the art. If desired, zsig63 polypeptide performance in this regard can be compared to digestive enzymes, such as amylase, lipase, proteases and the like. In addition, zsig63 polypeptides or agonists or antagonists thereof may be evaluated in combination with one or more digestive enzymes to identify synergistic effects.

The activity of molecules of the present invention can be measured using a variety of assays that measure stimulation of gastrointestinal cell contractility, modulation of nutrient uptake and/or secretion of digestive enzymes. Of particular interest are changes in contractility of smooth muscle cells. For example, the contractile response of segments of mammalian duodenum or other gastrointestinal smooth muscles tissue (Depoortere et al., *J. Gastrointestinal Motility* 30 1:150–159, 1989). An exemplary in vivo assay uses an ultrasonic micrometer to measure the dimensional changes radially between commissures and longitudinally to the plane of the valve base (Hansen et al., *Society of Thoracic Surgeons* 60:S384–390, 1995).

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–5 623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

Compounds identified as zsig63 agonists are useful in vitro and in vivo. For example, zsig63 and agonist compounds are useful as components of defined cell culture media, and may be used alone or in combination with other cytokines and hormones to replace serum that is commonly used in cell culture. Thus, zsig63 polypeptides and zsig63 agonist polypeptides are useful as a research reagent, such as for the expansion of cultured cells. As such, zsig63 polypeptides are added to tissue culture media for these cell types.

As a ligand, the activity of zsig63 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zsig63 polypeptide, its agonists, or antagonists. Preferably, the microphysiometer is used to measure responses of a zsig63-responsive eukaryotic cell, compared to a control eukaryotic cell that does not respond to zsig63 polypeptide. Zsig63-responsive eukaryotic cells comprise cells into which a receptor for zsig63 has been transfected creating a cell that is responsive to zsig63; or cells naturally responsive to zsig63 such as cells derived from, for example, pancreas, intestinal, prostate or tracheal tissue. Differences, measured by a change, for example, an increase or diminution in extracellular acidification, in the response of cells exposed to zsig63 polypeptide, relative to a control not exposed to zsig63, are a direct measurement of zsig63-modulated cellular responses. Moreover, such zsig63-modulated responses can be assayed under a variety of stimuli. Using the microphysiometer, there is provided a method of identifing agonists of zsig63 polypeptide, comprising providing cells responsive to a zsig63 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Moreover, culturing a third portion of the cells in the presence of zsig63 polypeptide and the absence of a test compound can be used as a positive control for the zsig63-responsive cells, and as a control to compare the agonist activity of a test compound with that of the zsig63 polypeptide. Moreover, using the microphysiometer, there is provided a method of identifying antagonists of zsig63 polypeptide, comprising providing cells responsive to a zsig63 polypeptide, culturing a first portion of the cells in the presence of zsig63 and the absence of a test compound, culturing a second portion of the cells in the presence of zsig63 and the presence of a test compound, and detecting a change, for example, an increase or a diminution in a cellular response of the second portion of the cells as compared to the first portion of the cells. The change in cellular response is shown as a measurable change extracellular acidification rate. Antagonists and agonists, for zsig63 polypeptide, can be rapidly identified using this method.

Moreover, zsig63 can be used to identify cells, tissues, or cell lines which respond to a zsig63-stimulated pathway. The microphysiometer, described above, can be used to rapidly identify ligand-responsive cells, such as cells responsive to zsig63 of the present invention. Cells can be cultured in the presence or absence of zsig63 polypeptide. Those cells which elicit a measurable change in extracellular acidification in the presence of zsig63 are responsive to zsig63. Such cells, can be used to identify antagonists and agonists of zsig63 polypeptide as described above.

zsig63 can also be used to identify inhibitors (antagonists) of its activity. Test compounds are added to the assays disclosed herein to identify compounds that inhibit the activity of zsig63. In addition to those assays disclosed herein, samples can be tested for inhibition of zsig63 activity within a variety of assays designed to measure receptor binding or the stimulation/inhibition of zsig63-dependent cellular responses. For example, zsig63-responsive cell lines can be transfected with a reporter gene construct that is responsive to a zsig63-stimulated cellular pathway. Reporter gene constructs of this type are known in the art, and will generally comprise a zsig63-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of zsig63 on the target cells as evidenced by a decrease in zsig63 stimulation of reporter gene expression. Assays of this type will detect compounds that directly block zsig63 binding to cell-surface receptors, as well as compounds that block processes in the cellular pathway subsequent to receptor-ligand binding. In the alternative, compounds or other samples can be tested for direct blocking of zsig63 binding to receptor using zsig63 tagged with a detectable label (e.g., $^{125}$I, biotin, horseradish peroxidase, FITC, and the like). Within assays of this type, the ability of a test sample to inhibit the binding of labeled zsig63 to the receptor is indicative of inhibitory activity, which can be confirmed through asecondary assays. Receptors used within binding assays may be cellular receptors or isolated, immobilized receptors.

A zsig63 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify zsig63 receptor, as an in vitro assay tool, or as a zsig63 antagonist. For use in assays, the chimeras are bound to a support via the $F_c$ region and used in an ELISA format.

Zsig63 polypeptides can also be used to prepare antibodies that bind to zsig63 epitopes, peptides or polypeptides. The zsig63 polypeptide or a fragment thereof serves as an antigen (immunogen) to inoculate an anirnal and elicit an immune response. One of skill in the art would recognize that antigenic, epitopebearing polypeptides contain a sequence of at least 6, preferably at least 9, and more preferably at least 15 to about 30 contiguous amino acid residues of a zsig63 polypeptide (e.g., SEQ ID NO:2). Polypeptides comprising a larger portion of a zsig63 polypeptide, i.e., from 30 to 10 residues up to the entire length of the amino acid sequence are included. Antigens or immunogenic epitopes can also include attached tags, adjuvants and carriers, as described herein. Suitable antigens include the zsig63 polypeptide encoded by SEQ ID NO:2 from amino acid number 16 (Ala) to amino acid number 219 (Gln), or a contiguous 9 to 204 amino acid fragment thereof. Other suitable antigens include domains 1, 2, and 3, and the acidic motif and coil-like region, as disclosed herein. Preferred peptides to use as antigens are hydrophilic peptides such as those predicted by one of skill in the art from a hydrophobicity plot. Zsig63 hydrophilic peptides include peptides comprising amino acid sequences selected from the group consisting of: amino acid residues 14 (Phe) to 19 (Arg) of SEQ ID NO: 2; amino acid residues 16 (Arg) to 21 (Phe) of SEQ ID NO: 2; amino acid residues 24 (Gly) to 29 (Asp) of SEQ ID NO: 2; amino acid residues 25 (Glu) to 30 (Asp) of SEQ ID NO: 2; and amino acid residues 187Glu) to 192 (Glu) of SEQ ID NO: 2. Moreover, polypeptides that comprise hydrophilic epitopes, such as those predicted from a Jameson-Wolf profile, are preferred antigens, and include: amino acid residues 24 (Gly) to 33 (Pro) of SEQ ID NO: 2; amino acid residues 17 (Lys) to 33 (Pro) of SEQ ID NO: 2; amino acid residues 66 (Thr) to 73 (Pro) of SEQ ID NO: 2; amino acid residues 103 (Pro) to 108 (Gly) of SEQ ID NO: 2; amino acid residues 190 (Ala) to 197 (Glu) of SEQ ID NO: 2; amino acid residues 202 (Lys) to 215 (Gly) of SEQ ID NO: 2; and amino acid residues 190 (Ala) to 215 (Glu) of SEQ ID NO: 2. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zsig63 polypeptide or a fiagment thereof. The immunogenicity of a zsig63 polypeptide may be increased through the use of an adjuvant, such as alum (aluminum hydroxide) or Freund's complete or incomplete adjuvant. Polypeptides useful for immunization also include fusion polypeptides, such as fusions of zsig63 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if antizsig63 antibodies herein bind to a zsig63 polypeptide, peptide or epitope with an affinity at least 10-fold greater than the binding affinity to control (non-zsig63) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Whether anti-zsig63 antibodies do not significantly cross-react with related polypeptide molecules is shown, for example, by the antibody detecting zsig63 polypeptide but not known related polypeptides using a standard Western blot analysis (Ausubel et al., ibid.). Examples of known related polypeptides are those disclosed in the prior art, such as known orthologs, and paralogs, and similar known members of a protein family, Screening can also be done using non-human zsig63, and zsig63 mutant polypeptides. Moreover, antibodies can be "screened against" known related polypeptides, to isolate a population that specifically binds to the zsig63 polypeptides. For example, antibodies raised to zsig63 are adsorbed to related polypeptides adhered to insoluble matrix; antibodies specific to zsig63 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoffet al., *Adv. in Immunol.* 43: 1–98, 1988; *Monoclonal Antibodies: Principles and Practice*, Goding, J. W. (eds.), *Academic Press Ltd.*, 1996; Benjamin et al., *Ann. Rev. Immunol.* 2: 67–101, 1984. Specifically binding anti-zsig63 antibodies can be detected by a number of methods in the art, and disclosed below.

A variety of assays known to those skilled in the art can be utilized to detect antibodies which bind to zsig63 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zsig63 protein or polypeptide.

Alternative techniques for generating or selecting antibodies useful herein include in vitro exposure of lymphocytes to zsig63 protein or peptide, and selection of antibody display libraries in phage or similar vectors (for instance, through use of immobilized or labeled zsig63 protein or peptide). Genes encoding polypeptides having potential zsig63 polypeptide binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zsig63 sequences disclosed herein to identify proteins which bind to zsig63. These "binding polypeptides" which interact with zsig63 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of zsig63 polypeptides; for detecting or quantitating soluble zsig63 polypeptides as marker of underlying pathology or disease. These binding polypeptides can also act as zsig63 antagonists to block zsig63 binding and signal transduction in vitro and in vivo. These antizsig63 binding polypeptides would be useful for inhibiting zsig63 activity or proteinbinding.

Antibodies to zsig63 may be used for tagging cells that express zsig63; for isolating zsig63 by affinity purification; for diagnostic assays for determining circulating levels of zsig63 polypeptides; for detecting or quantitating soluble zsig63 as marker of underlying pathology or disease; in analytical methods employing FACS; for screening expression libraries; for generating anti-idiotypic antibodies; and as neutralizing antibodies or as antagonists to block zsig63 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zsig63 or fragments thereof may be used in vitro to detect denatured zsig63 or fragments thereof in assays, for example, Western Blots or other assays known in the art.

Molecules of the present invention can be used to identify and isolate receptors for zsig63. For example, proteins and peptides of the present invention can be immobilized on a column and membrane preparations run over the column (*Immobilized Affinity Ligand Techniques*, Hermanson et al., eds., Academic Press, San Diego, Calif., 1992, pp. 195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Differentiation is a progressive and dynamic process, beginning with pluripotent stem cells and ending with terminally differentiated cells. Pluripotent stem cells that can regenerate without commitment to a lineage express a set of differentiation markers that are lost when cornmitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The novel polypeptides of the present invention may be useful for studies to isolate mesenchymal stem cells and myocyte or other progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, the present invention includes stimulating or inhibiting the proliferation of myocytes, smooth muscle cells, osteoblasts, adipocytes, chrondrocytes, neuronal and endothelial cells. Molecules of the present invention for example, may while stimulating proliferation or differentiation of cardiac myocytes, inhibit proliferation or differentiation of adipocytes, by virtue of the affect on their common precursor/stem cells. Thus molecules of the present invention may have use in inhibiting chondrosarcomas, atherosclerosis, restenosis and obesity.

Assays measuring differentiation include, for example, measuring cell markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference). Alternatively, zsig63 polypeptide itself can serve as an additional cell-surface or secreted marker associated with stage-specific expression of a tissue. As such, direct measurement of zsig63 polypeptide, or its loss of expression in a tissue as it differentiates, can serve as a marker for differentiation of tissues.

Similarly, direct measurement of zsig63 polypeptide, or its loss of expression in a tissue can be determined in a tissue or cells as they undergo tumor progression. Increases in invasiveness and motility of cells, or the gain or loss of expression of zsig63 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zsig63 expression. For example, appearance or disappearance of polypeptides that regulate cell motility can be used to aid diagnosis and prognosis of prostate cancer (Banyard, J. and Zetter, B. R., *Cancer and Metast Rev.* 17:449–458, 1999). As an effector of cell motility, zsig63 gain or loss of expression may serve as a diagnostic for prostate and other cancers.

Moreover, the activity and effect of zsig63 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly MS, et al. *Cell* 79: 315–328,1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing zsig63, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500–1800 mm³ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zsig63, on the ability of the tumor to recruit vasculature and undergo metastasis can thus be assessed. In addition, aside from using adenovirus, the implanted cells can be transiently transfected with zsig63. Use of stable zsig63 transfectants as well as use of induceable promoters to activate zsig63 expression in vivo are known in the art and can be used in this system to assess zsig63 induction of metastasis. Moreover, purified zsig63 or zsig63 conditioned media can be directly injected in to this mouse model, and hence be used in this system. For general reference see, O'Reilly M S, et al. *Cell* 79:315–328, 1994; and Rusciano D, et al. Murine Models of Liver Metastasis. *Invasion Metastasis* 14:349–361, 1995.

The activity of zsig63 and its derivatives (conjugates) on growth and dissemination of tumor cells derived from human hematologic malignancies can also be measured in vivo in a mouse Xenograft model Several mouse models have been developed in which human tumor cells are implanted into immunodeficient mice, collectively referred to as xenograft models. See Cattan, AR and Douglas, E *Leuk. Res.* 18:513–22, 1994; and Flavell, D J, *Hematological Oncology* 14:67–82, 1996. The characteristics of the disease model vary with the type and quantity of cells delivered to the mouse. Typically, the tumor cells will proliferate rapidly and can be found circulating in the blood and populating numerous organ systems. Therapeutic strategies appropriate for testing in such a model include antibody induced toxicity, ligand-toxin conjugates or cell-based therapies. The latter method, commonly referred to adoptive immunotherapy, involves treatment of the animal with components of the human immune system (i.e. lymphocytes, NK cells) and may include ex vivo incubation of cells with zsig63 or other immunomodulatory agents.

Polynucleotides encoding zsig63 polypeptides are useful within gene therapy applications where it is desired to increase or inhibit zsig63 activity. If a mammal has a mutated or absent zsig63 gene, the zsig63 gene can be introduced into the cells of the mammal. In one embodiment, a gene encoding a zsig63 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zsig63 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Ternin et al., U.S. Pat. No. 5,124,263; International Pat. Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zsig63 gene transcription, such as to inhibit cell proliferation in vivo. Polynucleotides that are complementary to a segment of a zsig63-encoding polynucleotide (e.g., a polynucleotide as set forth in SEQ ID NO:1) are designed to bind to zsig63-encoding mRNA and to inhibit translation of such mRNA. Such antisense polynucleotides are used to inhibit expression of zsig63 polypeptide-encoding genes in cell culture or in a subject.

Polynucleotides of the present invention are also used to detect abnormalities on human chromosome 4 associated with disease or other human traits. The polynucleotides of the present invention map to the 4q12–4q13 region on human chromosome 4. Zsig63 maps 3.15 cR__3000 from the framework marker WI-7844 on the chromosome 4 WICGR radiation hybrid map. Proximal and distal framework markers were WI-7844 and WI-4767, respectively. The use of surrounding markers positions zsig63 in the 4q12–4q13 region on the integrated LDB chromosome 4 map. (see Example 3).

The present invention also provides reagents which will find use in diagnostic applications. For example, the zsig63 gene, a probe comprising zsig63 DNA or RNA or a subsequence thereof can be used to determine if the zsig63 gene is present on chromosome 4 or if a mutation has occurred.

Detectable chromosomal aberrations at the zsig63 gene locus include but are not limited to aneuploidy, gene copy number changes, insertions, deletions, translocations, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel, et. al., ibid.; Marian, A. J., *Chest*, 108: 255–20 265, 1995). These methods can be employed to use zsig63 polynucleotides to detect abnormalities on human chromosome 4, such as those described below.

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene has.

Zsig63 is located at the 4q12–4q13 region of chromosome 4. Several genes of known function map to this region. Zsig63 polynucleotide probes can be used to detect abnormalities or genotypes associated with these defects. There are several genes that map to the zsig63 locus that are associated with human disease states, such as dental diseases: For example, Dentinogenesis imperfecta (4q13–q21) and dentin dysplasia, type II (4q) map near zsig63. As a salivary protein that also maps to this region of chromosome 4, defects in zsig63 may also play a role in dental disease, such as causing a defect in dental formation; and/or predisposition to dental carries and periodontal disease, as the saliva is important in maintaining a healthy microbial environment in the mouth. Moreover, a v-kit oncogene homolog related to Piebaldism and certain severe malignancies (e.g., certain leukemias) maps to 4q12 and is involved in common malignant gastrointestinal stromal tumors (GIST) tumors. As zsig63 maps to 4q12–q13 as well, there can be an association between loss of zsig63 function and tumor formation or progression. Moreover, translocations and duplications in 4q12 are seen in v-kit oncogene homolog related diseases. Thus, zsig63 polynucleotide probes can be used to detect abnormalities or genotypes associated with these diseases cancer susceptibility markers, as well as detection of chromosome translocations associated therewith. Because there is abundant evidence for cancer resulting from mutations in the 4q12 region, and zsig63 also maps to this chromosomal locus, mutations in zsig63 may also be directly involved in or associated with cancers, such as lymphoid cell cancers, gastrointestinal and salivary gland tumors, solid tumors or other tumors.

A diagnostic could assist physicians in determining the type of disease and appropriate associated therapy, or assistance in genetic counseling. As such, the inventive anti-zsig63 antibodies, polynucleotides, and polypeptides can be used for the detection of zsig63 polypeptide, rnRNA or anti-zsig63 antibodies, thus serving as markers and be directly used for detecting or genetic diseases or cancers, as described herein, using methods known in the art and described herein. Further, zsig63 polynucleotide probes can be used to detect abnormalities or genotypes associated with chromosome 4q12–q13 deletions and translocations associated with human diseases, such as those described above, or other translocations involved with malignant progression of tumors or other 4q12–q13 mutations, which are expected to be involved in chromosome rearrangements in malignancy; or in other cancers. Similarly, zsig63 polynucleotide probes can be used to detect abnormalities or genotypes associated with chromosome 4q12–q13 trisomy and chromosome loss associated with human diseases or spontaneous abortion. Moreover, amongst other genetic loci, those for Sarcoglycan linked muscular dystrophy (4q12), Stargardt Disease (4q), and others, all manifest themselves in human disease states as well as map to this region of the human genome. See the Online Mendellian Inheritance of Man (OMIM) gene map, and references therein, for this region of chromosome 4 on a publicly available WWW server (http:I/www3.ncbi.nlm.nih.gov/ htbin-post/Omim/getmap?chromosome=4q12). All of these serve as possible candidate genes for an inheritable disease which show linkage to the same chromosomal region as the zsig63 gene. Thus, zsig63 polynucleotide probes can be used to detect abnormalities or genotypes associated with these defects.

A diagnostic could assist physicians in determining the type of disease and appropriate associated therapy, or assistance in genetic counseling. As such, the inventive anti-zsig63 antibodies, polynucleotides, and polypeptides can be used for the detection of zsig63 polypeptide, MRNA or anti-zsig63 antibodies, thus serving as markers and be directly used for detecting or genetic diseases or cancers, as described herein, using methods known in the art and described herein. Further, zsig63 polynucleotide probes can be used to detect abnormalities or genotypes associated with chromosome 4q12–q13 deletions and translocations associated with human diseases, or other translocations involved with malignant progression of tumors or other 4q12–q13 mutations, which are expected to be involved in chromosome rearrangements in malignancy; or in other cancers. Similarly, zsig63 polynucleotide probes can be used to detect abnormalities or genotypes associated with chromosome 4q12–q13 trisomy and chromosome loss associated with human diseases or spontaneous abortion. Thus, zsig63 polynucleotide probes can be used to detect abnormalities or genotypes associated with these defects.

Similarly, defects in the zsig63 gene itself may result in a heritable human disease state. Molecules of the present invention, such as the polypeptides, antagonists, agonists, polynucleotides and antibodies of the present invention would aid in the detection, diagnosis prevention, and treatment associated with a zsig63 genetic defect. As discussed above, defects in the zsig63 gene itself may result in a heritable human disease state or increase susceptibility to certain diseases. Molecules of the present invention, such as the polypeptides, antagonists, agonists, polynucleotides and antibodies of the present invention would aid in the detection, diagnosis prevention, and treatment associated with a zsig63 genetic defect. In addition, zsig63 polynucleotide probes can be used to detect allelic differences between diseased or non-diseased individuals at the zsig63 chromosomal locus. As such, the zsig63 sequences can be used as diagnostics in forensic DNA profiling.

In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zsig63 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zsig63 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zsig63 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, MRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO: 1, the complement of SEQ ID NO: 1, or an RNA equivalent thereof. Such methods of showing genetic linkage analysis to human disease phenotypes are well known in the art. For reference to PCR based methods in diagnostics see see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zsig63 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, Chest 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis*, Vol. 2: *Detecting Genes* (Cold Spring Harbor Laboratory Press 1998), Dracopoli et al (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)). Direct analysis of an zsig63 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Mice engineered to express the zsig63 gene, referred to as "transgenic mice," and mice that exhibit a complete absence of zsig63 gene function, referred to as "knockout mice," may also be generated (Snouwaert et al., *Science* 257:1083, 1992; Lowell et al., *Nature* 366:740–42, 1993; Capecchi, M.R., Science 244: 1288–1292, 1989; Palmiter, R. D. et al. *Annu Rev Genet*. 20: 465–499, 1986). For example, transgenic mice that over-express zsig63, either ubiquitously or under a tissue-specific or tissue-restricted promoter can be used to ask whether over-expression causes a phenotype. For example, over-expression of a wild-type zsig63 polypeptide, polypeptide fragment or a mutant thereof may alter normal cellular processes, resulting in a phenotype that identifies a tissue in which zsig63 expression is functionally relevant and may indicate a therapeutic target for the zsig63, its agonists or antagonists. For example, a preferred transgenic mouse to engineer is one that over-expresses the zsig63 mature polypeptide (approximately amino acids 16 (Ala) to 219 (Gln) of SEQ ID NO:2). Moreover, such over-expression may result in a phenotype that shows similarity with human diseases. Similarly, knockout zsig63 mice can be used to determine where zsig63 is absolutely required in vivo. The phenotype of knockout mice is predictive of the in vivo effects of that a zsig63 antagonist, such as those described herein, may have. The human zsig63 cDNA can be used to isolate murine zsig63 mRNA, cDNA and genomic DNA, which are subsequently used to generate knockout mice. These mice may be employed to study the zsig63 gene and the protein encoded thereby in an in vivo system, and can be used as in vivo models for corresponding human diseases. Moreover, transgenic mice expression of zsig63 antisense polynucleotides or ribozymes directed against zsig63, described herein, can be used analogously to transgenic mice described above.

For pharmaceutical use, the proteins of the present invention are formulated for topical, inhalant or parenteral, particularly intravenous or subcutaneous, delivery according to conventional methods. Intravenous administration will be by bolus injection or infusion over a typical period of one to several hours. In general, pharmaceutical formulations will include a zsig63 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLE 1

Identification of zsig63

Using an EST Sequence to Obtain Full-length zsig63

Scanning of a translated DNA database resulted in identification of an expressed sequence tag (EST) sequence found to be a novel member of the adhesion family and designated zsig63.

Confirmation of the EST sequence was made by sequence analyses of the cDNA from which the EST originated. This cDNA clone was obtained and sequenced using the following primers: ZC6768 (SEQ ID NO:4), ZC694 (SEQ ID NO:5), ZC7231 (SEQ ID NO:6), ZC7764a (SEQ ID NO:7). The insert was about 1 kb and was full-length.

EXAMPLE 2

Tissue Distribution

Northern blot analysis was performed using Human Multiple Tissue Northern™ Blots (MTN I, MTN II, MTN III) (Clontech) and an in-house Northern blot prepared using 2 mg each of human testis, prostate spinal cord, salivary gland, thymus, and thyroid poly-A+RNA (Clontech). The plasmid containing full-length zsig63 (Example 1) was digested as per manufacturer's instructions with HindIII and Xbal (New England BioLabs, Beverly, Mass.) for 2 hours at 37° C. A sample of the digested plasmid DNA was run on a 1% agarose gel. A band of the expected size of 662 bp was seen. The 662 bp fragment, was gel purified using a commercially available kit (QiaexII™; Qiagen) and then radioactively labeled with $^{32}$P-dCTP using Rediprime ™ (Amersham), a random prime labeling system, according to the manufacturer's specifications. The probe was then purified using a Nuc-Trap™ column (Stratagene) according to the manufacturer's instructions. ExpressHyb™ (Clontech) solution was used for prehybridization and as a hybridizing solution for the Northern blots. Hybridization took place overnight at 65° C. using 1–2×10$^6$ cpm/ml of labeled probe. The blots were then washed 4 times for 20 minutes in 2×SSC/0.1% SDS at 25° C., and then twice more in 0.1×SSC/0.1% SDS at 50° C. for 30 minutes each. A transcript of approximately 1.3 kb was detected at very high levels in salivary gland, and moderate to low levels in thyroid and prostate.

Dot Blots were also performed using Human RNA Master Blots™ (Clontech). The methods and conditions for the Dot Blots are the same as for the Multiple Tissue Blots described above. Dot blot had a very strong signal in salivary gland.

EXAMPLE 3

Chromosomal Mapping of the zsig63 Gene

Zsig63 was mapped to chromosome 4 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zsig63 with the "GeneBridge 4 RH Panel", 20 μl reactions were set up in a 96-well microtiter plate (Stratagene, La Jolla, Calif.) and used in a "RoboCycler Gradient 96" thermal cycler (Stratagene). Each of the 95 PCR reactions consisted of 2 μl 10×KlenTaq PCR reaction buffer (Clontech Laboratories, Inc., Palo Alto, Calif.), 1.6 μl dNTPs mix (2.5 mM each, Perkin-Elmer, Foster City, Calif.), 1 μl sense primer, ZC 20,555, (SEQ ID NO:8) 1 μl antisense primer, ZC 20,556, (SEQ ID NO:9) 2 μl "Redi-Load" (Research Genetics, Inc., Huntsville, Ala.), 0.4 μl 5×Advantage KlenTaq Polymerase Mix (Clontech), 25 ng of DNA from an individual hybrid clone or control and ddH$_2$O for a total volume of 20 μl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 58° C. and 1 minute and 15 seconds extension at 72° C., followed by a final 1 cycle extension of 7 minutes at 72° C. The reactions were separated by electrophoresis on a 2% agarose gel (Life Technologies, Gaithersburg, Md.).

The results showed that zsig63 maps 3.15 cR_3000 from the framework marker WI-7844 on the chromosome 4 WICGR radiation hybrid map. Proximal and distal framework markers were Wl-7844 and WI-4767, respectively. The use of surrounding markers positions zsig63 in the 4q12–4q13 region on the integrated LDB chromosome 4 map (The Genetic Location Database, University of Southhampton, WWW server: http:l/cedar.genetics.soton.ac.uk/public_html/).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. An isolated polynucleotide wherein the polynucleotide hybridizes to the 4q12–4q13 region of human chromosome 4 under hybridization wash conditions of 0.1×SSC to 2×SSC, 0.1% SDS at 55–65° C. encoding a polypeptide that comprises a sequence of amino acid residues selected from the group consisting of:

(a) the amino acid sequence as shown in SEQ ID NO: 2 from amino acid number 16 (Arg) to amino acid number 37 (Ser);

(b) the amino acid sequence as shown in SEQ ID NO: 2 from amino acid number 38 (Leu) to amino acid number 126 (Ala);

(c) the amino acid sequence as shown in SEQ ID NO: 2 from amino acid number 127 (Pro) to amino acid number 219 (Gln);

(d) the amino acid sequence as shown in SEQ ID NO:2 from amino acid number 16 (Arg) to amino acid number 219 (Gln); and (e) the amino acid sequence as shown in SEQ ID NO:2 from amino acid number 1 (Met) to amino acid number 219 (Gln).

2. An isolated polynucleotide comprising a polynucleotide which hybridizes to the 4q12–4q13 region of human chromosome 4 under hybridization wash conditions of 0.1× SSC to 2×SSC, 0.1% SDS at 55–65° C. that is selected from the group consisting of:
(a) the polynucleotide sequence as shown in SEQ ID NO:1 from nucleotide 173 to nucleotide 238;
(b) the polynucleotide sequence as shown in SEQ ID NO:1 from nucleotide 239 to nucleotide 505;
(c) the polynucleotide sequence as shown in SEQ ID NO:1 from nucleotide 506 to nucleotide 784;
(d) the polynucleotide sequence as shown in SEQ ID NO:1 from nucleotide 173 to nucleotide 784;
(e) the polynucleotide sequence as shown in SEQ ID NO:1 from nucleotide 128 to nucleotide 784; and
(f) the polynucleotide sequence complementary to (a) through (e).

3. An isolated polynucleotide sequence according to claim 1, wherein the polynucleotide comprises nucleotide 1 to nucleotide 657 of SEQ ID NO:3.

4. An expression vector comprising the following operably linked elements:
a transcription promoter;
a DNA segment wherein said segment hybridizes to the 4q12–4q13 region of human chromosome 4 under hybridization wash conditions of 0.1×SSC to 2×SSC, 0.1% SDS at 55–65° C. encoding a polypeptide comprising an amino acid sequence shown in SEQ ID NO:2 from amino acid number 16 (Arg) to amino acid number 219 (Gln); and
a transcription terminator.

5. An expression vector according to claim 4, further comprising a secretory signal sequence operably linked to the DNA segment.

6. A cultured cell into which has been introduced an expression vector according to claim 4, wherein the cell expresses a polypeptide encoded by the DNA segment.

7. A DNA construct encoding a fusion protein, the DNA construct comprising:

a first DNA segment wherein said segment hybridizes to the 4q12–4q13 region of human chromosome 4 under hybridization wash conditions of 0.1×SSC to 2×SSC, 0.1% SDS at 55–65° C. encoding a polypeptide selected from the group consisting of:
(a) the amino acid sequence of SEQ ID NO: 2 from residue number 1 (Met) to residue number 15 (Ala);
(b) the amino acid sequence of SEQ ID NO:2 from residue number 16 (Arg) to residue number 219 (Gln); and
at least one other DNA segment encoding an additional polypeptide, wherein the first and other DNA segments are connected in-frame; and
encode the fusion protein.

8. A method of producing a zsig63 polypeptide comprising:
culturing a cell according to claim 6; and
isolating the zsig63 polypeptide produced by the cell.

9. An isolated polynucleotide wherein the polynucleotide hybridizes to the 4q12–4q13 region of human chromosome 4 under wash conditions of 0.1×SSC to 2×SSC, 0.1% SDS at 55–65° C. encoding a polypeptide consisting of a sequence of amino acid residues selected from the group consisting of:
(a) the amino acid sequence of SEQ ED NO:2 from residues number 16 (Arg) to residue number 37 (Ser);
(b) the amino acid sequence of SEQ ID NO:2 from residues number 38 (Leu) to residue number 126 (Ala);
(c) the amino acid sequence of SEQ ID NO:2 from residues number 127 (Pro) to residue number 219 (Ser);
(d) the amino acid sequence of SEQ ID NO:2 from residues number 16 (Arg) to residue number 219 (Gln) "; and
(e) the amino acid sequence of SEQ ID NO:2 from residues number 1 (Met) to residue number 219 (Gln).

* * * * *